US008921614B1

(12) United States Patent
Davis et al.

(10) Patent No.: US 8,921,614 B1
(45) Date of Patent: Dec. 30, 2014

(54) SELECTIVE DEOXYGENATION OF HYDROXYBENZALDEHYDES

(71) Applicant: United States of America as Represented by the Secretary of the Navy, Washington, DC (US)

(72) Inventors: Matthew C. Davis, Ridgecrest, CA (US); Benjamin G. Harvey, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/202,094

(22) Filed: Mar. 10, 2014

Related U.S. Application Data

(63) Continuation-in-part of application No. 14/172,673, filed on Feb. 4, 2014.

(60) Provisional application No. 61/778,705, filed on Mar. 13, 2013, provisional application No. 61/769,297, filed on Feb. 26, 2013.

(51) Int. Cl.
*C07C 37/055* (2006.01)
*C07C 37/20* (2006.01)
*C07C 39/21* (2006.01)

(52) U.S. Cl.
CPC .................. *C07C 37/20* (2013.01); *C07C 39/21* (2013.01)
USPC ........................................ 568/729

(58) Field of Classification Search
CPC ...................................................... C07C 37/055
USPC .......................................................... 568/729
See application file for complete search history.

(56) References Cited

U.S. PATENT DOCUMENTS

| 4,087,336 A | 5/1978 | Wagenknecht |
| 8,101,804 B2 * | 1/2012 | Schouteeten et al. ......... 568/309 |

FOREIGN PATENT DOCUMENTS

| CN | 1736986 A | 2/2006 |

OTHER PUBLICATIONS

Database CAPLUS on STN, Acc. No. 1941:8752, Takaoka, Proceedings of the Imperial Academy (Tokyo) (1940), 16, pp. 405-407 (abstract).*
Dieguez, H. R. et al. J. Am. Chem. Soc. 2010, 132, 254-259 describes the synthesis of 3,3'-5,5'tetramethoxystilbene via Cp2TiCl mediated reductive coupling.

* cited by examiner

*Primary Examiner* — Brian J Davis
(74) *Attorney, Agent, or Firm* — Charlene A. Haley

(57) ABSTRACT

A method for selective deoxygenation of hydroxybenzaldehydes including, condensing syringaldehyde (3,5-dimethoxy-4-hydroxybenzaldehyde) and a functionalized phenylacetic acid with at least one first base and at least one anhydride to produce an arylcinnamic acid, decarboxylating of said arylcinnamic acid with at least one decarboxylation catalyst at temperatures ranging from about 30° C. to 200° C. or thermally at temperatures ranging from about 100° C. to 350° C. to produce a first stilbene, hydrodeoxygenating the stilbene by conversion to a sulfonate in the presence of at least one second base in water or at least one organic solvent to yield a sulfonate reducing the sulfonate(s) with a reductive elimination catalyst to produce a second stilbene, and reacting the second stilbene with a hydrolyzing agent to generate a polyphenol.

14 Claims, 1 Drawing Sheet

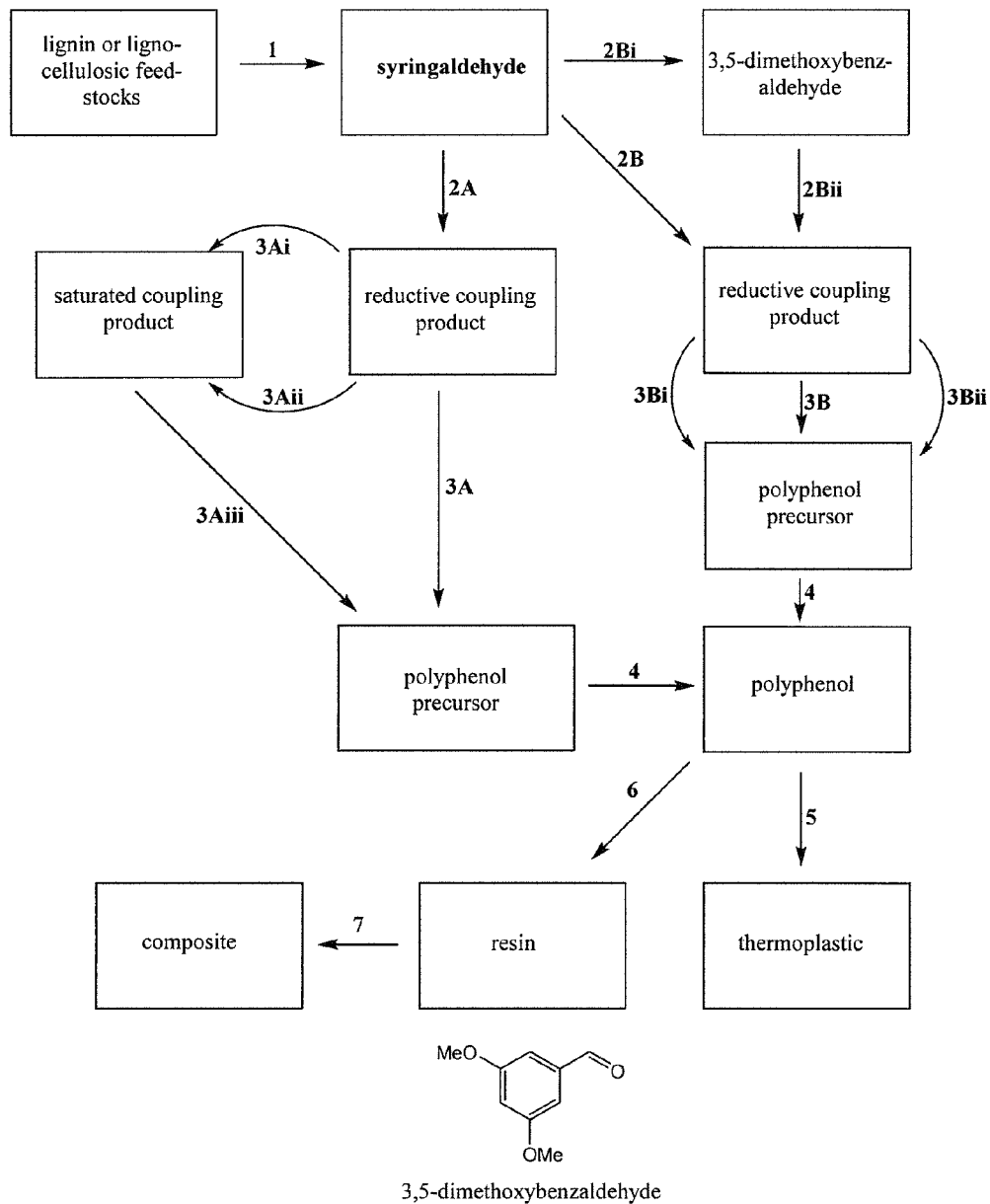

SELECTIVE DEOXYGENATION OF HYDROXYBENZALDEHYDES

CROSS-REFERENCE TO RELATED APPLICATIONS

This is a non-provisional patent application, claiming the benefit of, parent application Ser. No. 61/778,705 filed on Mar. 13, 2013 and is a continuation-in-part of Ser. No. 61/769,297 filed Feb. 26, 2013 and its non-provisional application Ser. No. 14/172,673 filed on Feb. 4, 2014, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to methods to synthesize renewable precursors to high temperature thermosetting resins useful for fabrication of low-weight, composite aerospace structures.

BRIEF DESCRIPTION OF THE DRAWING

FIG. 1 is a flow chart showing methods to synthesize renewable precursors to high temperature thermosetting resins useful for fabrication of low-weight, composite aerospace structures, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

The invention generally relates to the synthesis of renewable precursors to high temperature thermosetting resins useful for fabrication of low-weight, composite aerospace structures.

Embodiments of the invention generally relate to methods for the selective deoxygenation of hydroxybenzaldehydes including, condensing syringaldehyde (3,5-dimethoxy-4-hydroxybenzaldehyde) and a functionalized phenylacetic acid with at least one first base and at least one anhydride to produce an arylcinnamic acid, decarboxylating of the arylcinnamic acid with at least one decarboxylation catalyst at temperatures ranging from about 30° C. to 200° C., or thermally at temperatures ranging from about 100° C. to 350° C. to produce a first stilbene, hydrodeoxygenating the stilbene by conversion to a sulfonate in the presence of at least one second base in water or at least one organic solvent to yield a sulfonate, reducing the sulfonate(s) with a reductive elimination catalyst to produce a second stilbene, and reacting the second stilbene with a hydrolyzing agent to generate a polyphenol.

In embodiments, the functionalized phenylacetic acid is, but not limited to, 4-methoxyphenylacetic acid. In embodiments, the arylcinnamic acid is, but not limited to, 2-arylcinnamic acid. In embodiments, the decarboxylation catalyst is selected from the group consisting of, but not limited to, 1-methylimidazolium, p-toluenesulfonate, other ionic liquids, Cu-based catalysts, silver based catalysts, amine catalysts, and any combination thereof. In embodiments, the reductive elimination catalyst is selected from a group consisting of, but not limited to, low valent Ni or Pd compounds. In embodiments, the first stilbene is, but not limited to, a trans-isomer(s). In embodiments, the phenylacetic acid has one or more hydroxy or alkoxy groups at any position(s) on the aromatic ring.

In embodiments, the base is selected from the group consisting of, but not limited to, pyridine, other aromatic amines, triethylamine, other alkyl amines, alkali or alkaline earth alkoxides, phosphates, carbonates, and any combination thereof. In embodiments, the organic solvent is selected from the group consisting of, but not limited to, methylene chloride, chloroform, diethyl ether, tetrahydrofuran, other solvents capable of dissolving aromatic triflates and any combination thereof. In embodiments, the second stilbene is, but not limited to, resveratrol trimethyl ether. In embodiments, the agent is selected from the group consisting of, but not limited to, molten pyridine hydrochloride, mineral acids, $BBr_3$, and $BCl_3$.

Embodiments further include methylating the first stilbene with an alkali alkoxide and iodomethane to produce (E)-3,4,5,4'-tetramethoxystilbene. In embodiments, the 2-arylcinnamic acid is

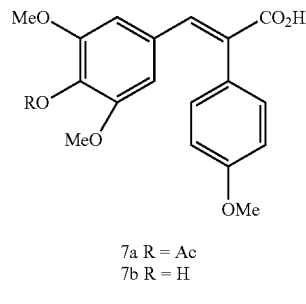

7a R = Ac
7b R = H where R is acetyl or hydrogen and where sulfonate is

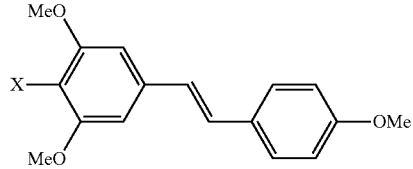

where x is selected from the group consisting of, but not limited to, $—OSO_2CH_3$, $—OSO_2(C_6H_4)CH_3$, and $OSO_2CF_3$. Another aspect of the invention relates to trans-resveratrol produced by the method herein.

Sulfonates of phenolic aldehydes or phenolic stilbenes can be selectively hydrodeoxygenated whereby the aldehyde and/or stilbene moiety is intact allowing for further chemical transformations. The technology was used to generate resveratrol and DMU-212 by unique and commercially viable processes.

Syringaldehyde and vanillin are hydroxybenzaldehydes that can be generated from lignin through a variety of thermochemical and catalytic methods. These benzaldehydes and other related compounds can also be derived from spent liquor generated by the process of paper pulping. The type of lignin or wood used as a feedstock results in the isolation of variable amounts of syringaldehyde and vanillin. These renewable molecules have great potential for the preparation of high value phenolic compounds, but the effective utilization of multifunctional benzaldehydes requires selective deoxygenation methods. This invention teaches how to remove the hydroxyl groups of syringaldehyde and vanillin to give 3,5-dimethoxybenzaldehyde or 3-methoxybenzaldehyde, respectively. The latter is useful as a starting material for the manufacture of many other products including resveratrol, a natural product that has potential as an anticancer compound.

References: Clauss. K.; Jensen. H. Hydrogenative removal of phenolic hydroxyl groups. Angew. Chem. Intt. Ed. 1973. 12, 918; Hu. T. Q.; Cairns. O. R.; James, B. R. Removal of phenolic hydroxyl groups in lignin model compounds and its effect on photostability. Holzforschung 2000, 54.127-132.

1. Hydroxybenzaldehydes are first converted into sulfonates.
2. Sulfonates are reduced by a catalyst mixture—as an example: (a palladium II salt), diphosphine ligand (DPPF, DPPP, DPPE, etc) and reducing agent (a formate salt) to give benzaldehydes.

A key advantage of the current process: The invention teaches that the sulfonate of a specific hydroxystilbene molecule can be selectively reduced by the said process. In this way, the stilbene double bond remains intact while the hydroxy group is removed. This stilbene product is an important chemical intermediate and will allow for a new manufacturing process for the natural product resveratrol that may be important as an anticancer compound.

When a starting material is being contemplated for the synthesis of an active pharmaceutical ingredient or a building block for polymers, natural products are the green alternatives to petroleum feedstocks. Plant metabolites are an excellent source for aromatic compounds but are invariably oxygenated. In certain cases, the hydroxy groups of the natural products are ideally located and can be simply built upon or protected to allow for chemical modification elsewhere in the molecule. More often, the natural product has too many hydroxy groups or it would be preferable to replace one or more of them with some other group. This specification describes a general method for the hydrodeoxygenation of some phenolic compounds (Ph-OH→Ph-H) by reduction of the corresponding trifluoromethanesulfonates (triflates) in an effort to synthesize the natural polyphenol resveratrol (trans 3,4',5-trihydroxystilbene), a compound which may have biological activity in mammals.

The spent liquor from paper processing mills contains variable amounts of the aromatic aldehydes vanillin (3-methoxy-4-hydroxybenzaldehyde, 1a) and syringaldehyde (3,5-dimethoxy-4-hydroxybenzaldehyde, 1b) depending on the source of wood (conifer or deciduous). Syringaldehyde is very close in structure to one of the typical starting materials for resveratrol synthesis, namely 3,5-dimethoxybenzaldehyde (3b). The triflates of vanillin (2a) and syringaldehyde (2b) were obtained by reaction with trifluoromethanesulfonic anhydride using pyridine as base in methylene chloride in high yields (Scheme 1). Triflate 2a was

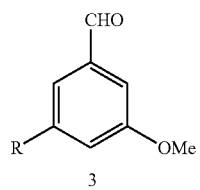

a) R = H b) R = OMe isolated as an oil. The reduction procedure employed was based on a homogeneous method established by Cacchi et al. using palladium acetate and a phosphine ligand along with a reducing agent in dimethylformamide solvent. (S. Cacchi, E. Morera and G. Ortar, *Tetrahedron Lett.*, 25, 4821 (1984).) However, with the formic acid salt of triethylamine as the hydrogen donor and triphenylphosphine as ligand, only starting material was recovered after the reaction. The careful studies of Cabri et al. later established the critical role bidentate phosphine ligands play in the reaction. (W. Cabri, S. DeBernardinis, F. Francalanci and S. Penco, *J. Org. Chem.*, 55, 350 (1990): Y. Pan and C. P. Holmes, *Org. Lett.*, 3, 2769 (2001): J. M. Saá, M. Dopico, G. Martorell and A. Garcia-Raso, *J. Org. Chem.*, 55, 991 (1990)). The reduction proceeded very smoothly to give the aldehydes 3a and 3b in high yield using 1,1-bis(diphenylphosphino)ferrocene (DPPF) all else being the same. Although expensive due to the price of Tf$_2$O, this rapid preparation of aldehyde 3b may be attractive for laboratory scale natural product synthesis. Otherwise, the compound is made by a five-step route starting from benzoic acid, the last step of which is a stoichiometric, heavy metal-mediated oxidation to carboxaldehyde which can be capricious. Rather than repeat the conversion of 3b to resveratrol, an attempt was made to expand the scope of this triflate reduction (Scheme 2). Perkin condensation of syringaldehyde (1b) and 4-methoxyphenylacetic acid (4) gave, after hydrolysis of the intermediate acetate ester, a good yield of the previously unreported 2-arylcinnamic acid 5.

Scheme 2

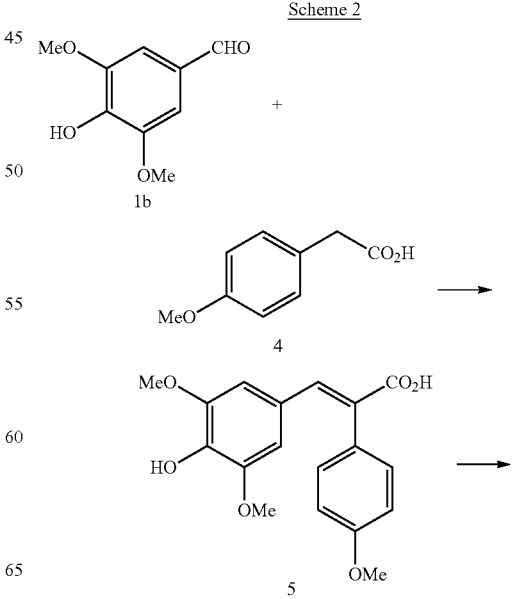

Scheme 1

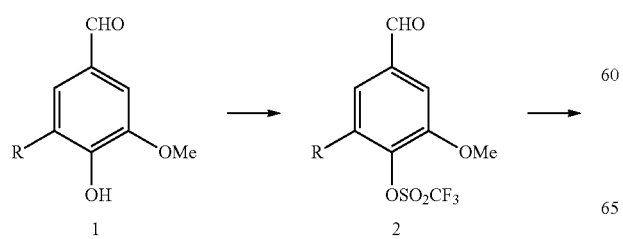

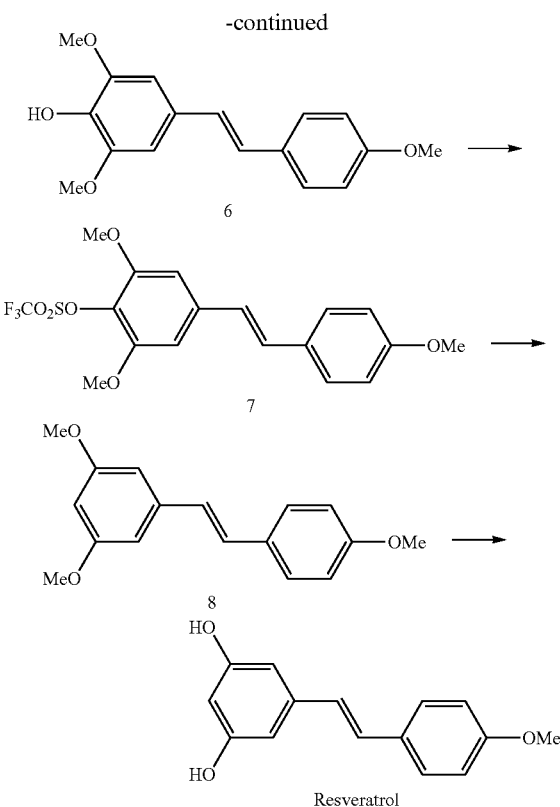

Because the alkene hydrogen of 5 appeared downfield (δ7.66), it was believed to be the trans regioisomer, a fact confirmed by X-ray crystallographic analysis. Crystallographic data (without structure factors) for compound 5 has been deposited with Cambridge Crystallographic Data Centre as supplementary publication CCDC 888230)).

Rather than the conventional method of copper and quinoline for the decarboxylation of 5, the interesting conditions with ionic liquids of Sharma et al. were adopted. (A. Sharma, R. Kumar, N. Sharma, V. Kumar and A. K. Sinha, *Adv. Synth. Catal.,* 350, 2910 (2008)). Microwave irradiation, however, was not necessary and simple heating of 5 to ~130° C. in the melt of the protic ionic liquid 1-methylimidazolium p-toluenesulfonate gave an excellent yield of stilbene 6, mp. 110-112° C. Incidentally, Sharma et al. described the preparation of 6 by the Heck reaction between 2,6-dimethoxy-4-vinylphenol and 4-iodoanisole. (A. Sharma, N. Sharma, R. Kumar, A. Shard and A. K. Sinha, *Chem. Comm.,* 3283 (2010)). They indicated the trans geometry for their product melting at 96-98° C., although the J coupling constant of the alkene protons could not be observed due to overlapping signals. Using DMSO as NMR solvent for 6, the alkene vicinal coupling of 16 Hz is clearly visible which is typical for trans geometry. So these conditions not only brought about decarboxylation but, fortuitously, isomerized the stilbene to the thermodynamically favored trans isomer presumably by way of a quinone-type resonance contributor.

The hydrodeoxygenation of 6 was carried out in the same manner as previously described for 1a and 1b. Triflate 7 underwent reduction to the stilbene 8 (resveratrol trimethyl ether) without concomitant reduction of the double bond. This result was surprising since several groups have reduced stilbenes to bibenzyls by catalytic transfer hydrogenation using formate salts and homogeneous or heterogeneous palladium catalyst. However, Brunel did report the failure of alkene reduction when bidentate phosphine ligands were employed. (J. M. Brunel, *Synlett,* 330 (2007)

The synthesis of resveratrol was completed by refluxing a mixture of 8 in the molten salt pyridine hydrochloride.

Although this reagent is convenient to work with, the yield of the dealkylation was poor which, based on other work, is most likely caused by oligomerization. Other reagents can be utilized to accomplish this step cleanly (including $BBr_3$ or $BCl_3$).

Since 6 (DMU-291) is the putative active metabolite of the anticancer compound DMU-212 (9), the latter was prepared by simple methylation of 6, using potassium tert-butoxide and iodomethane (Scheme 3), and the product was fully characterized adding further value to the synthetic pathway described here.

Scheme 3

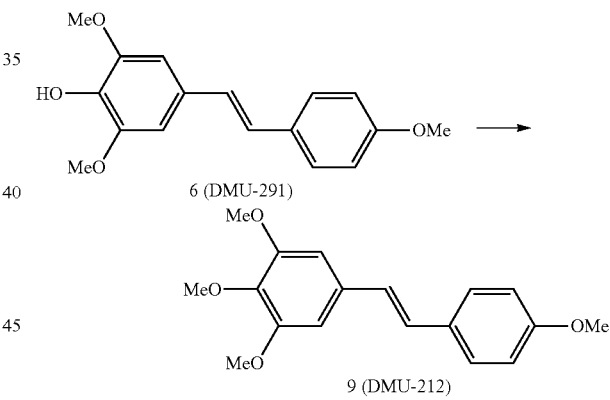

Scheme 4

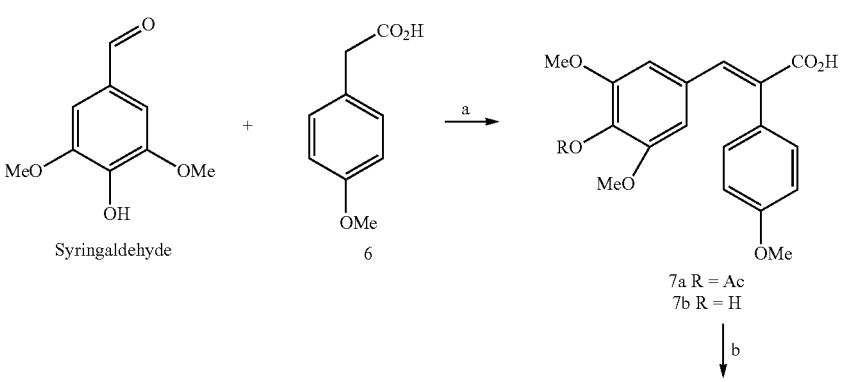

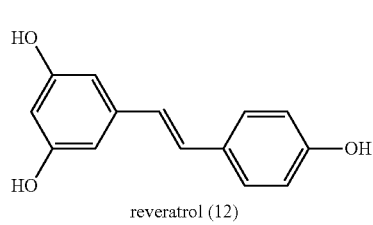

reveratrol (12)

-continued

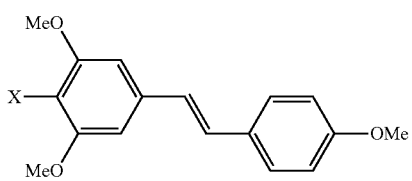

8 X = OH
9 X = OSO₂CF₃
10 X = H
11 X = OMe

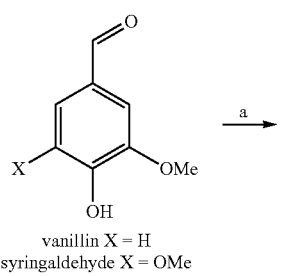

vanillin X = H
syringaldehyde X = OMe

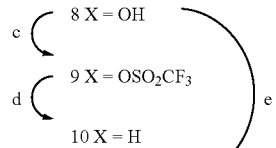

1 X = H
2 X = OMe

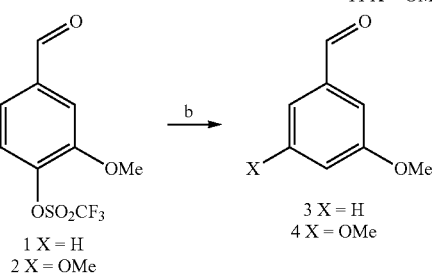

3 X = H
4 X = OMe

In conclusion, the triflates of hydroxybenzaldehydes undergo palladium-catalyzed deoxygenation without reduction of the carbonyl group. Syringaldehyde, which can be obtained from the spent liquor of paper processing, was converted into resveratrol in five steps in 12% overall yield (unoptimized).

Three benefits of the process: 1) The process starts from a cheap and renewable phenol (syringaldehyde) that can be isolated from various biomass sources, and obtained as a byproduct of paper production or conversion of lignocellulosic feedstocks to biofuels. 2) The process is selective for the trans-isomer. 3) The decarboxylation does not require a copper catalyst.

Experimental Section:

The melting points were acquired on a Meltemp II electrothermal capillary melting point apparatus (Laboratory Devices, Holliston, Mass.) and are not corrected. All NMR data were obtained on a Bruker Avance II 300 MHz spectrometer ($^1$H at 300 MHz, $^{13}$C at 75 MHz, $^{19}$F at 282 MHz). NMR data (free induction decay signals) were processed using NUTS software from Acorn NMR (Livermore, Calif.). All $^1$H, $^{13}$C and $^{19}$F spectra are referenced to solvent, tetramethylsilane or fluorotrichloromethane, respectively. In all cases, thin-layer chromatography (TLC) was carried out on aluminum foil backed, silica gel plates eluting with a mixture of hexanes/EtOAc. Trifluoromethanesulfonic anhydride (Tf₂O), syringaldehyde (1b), vanillin (1a), 4-methoxyphenylacetic acid (4), anhydrous N,N-dimethylformamide (DMF), 1,1'-bis(diphenylphosphino)ferrocene (DPPF) and all other reagents were obtained commercially.

3-Methoxy-4-(trifluoromethanesulfonyloxy)benzaldehyde (2a)

To a round-bottomed flask equipped with magnetic stir bar was charged 1a (3.0 g, 20 mmol), pyridine (4.7 g, 59 mmol, 3 equiv) and CH₂Cl₂ (25 mL). The mixture was cooled in a dry ice-acetone bath and Tf₂O (6.6 mL, 11.1 g, 39 mmol, 2 equiv) was added dropwise over 30 min Afterwards, the mixture was stirred at room temperature for 2 h. The reaction mixture was washed with H₂O (2×25 mL) followed by brine (25 mL). The organic phase was separated, dried over anhydrous MgSO₄ and evaporated under reduced pressure leaving a brownish oil (5.12 g, 90%). The crude product could be further purified by short-path distillation at reduced pressure (0.1 ton) to give the product as colorless oil. However, the compound appears to be heat sensitive as there was a significant decomposition residue in the distillation pot. $^1$H NMR (CDCl₃): δ 9.98 (s, 1H), 7.56 (d, J=1.7 Hz, 1H), 7.51 (dd, J=8.2 and 1.8 Hz, 1H), 7.40 (d, J=8.0 Hz, 1H), 3.99 (s, 3H); $^{13}$C NMR (CDCl₃): δ 190.53, 152.49, 142.97, 137.06, 124.27, 123.45, 121.06, 118.92 (q, $^1J_{CF}$=321.5 Hz), 112.06, 56.75; $^{19}$F {$^{13}$C} NMR (CDCl₃): δ −74.2. The product was used in the synthesis of compound 3a without further purification.

3,5-Dimethoxy-4-(trifluoromethanesulfonyloxy)benzaldehyde (2b)

To a round-bottomed flask (100 mL) equipped with magnetic stir bar and addition funnel (10 mL) was charged 1b (3.0 g, 16.5 mmol), CH₂Cl₂ (50 mL) and triethylamine (3.3 g, 33 mmol, 2 equiv). The mixture was cooled to 0° C. in an ice bath. The funnel was charged with Tf₂O (6.9 g, 4.18 mL, 24.8 mmol, 1.5 equiv) which was added dropwise over 1 h. After several hours at 0° C., the mixture was allowed to warm up to room temperature and washed with H₂O. The organic phase was washed with brine (25 mL), separated and dried over anhydrous MgSO₄. The organic phase was treated with decolorizing charcoal, filtered and evaporated under reduced pressure. Compound 2b was obtained as colorless crystals by recrystallization from hexanes (4.5 g, 87%), mp. 105-107° C., lit.[21] 108-110° C. $^1$H NMR (CDCl₃): δ 9.95 (s, 1H), 7.17 (s, 2H), 3.99 (s, 6H); $^{13}$C NMR (CDCl₃): δ 190.65, 153.45, 136.13, 132.25, 118.85 (q, $^1J_{CF}$=321.2 Hz), 106.15, 56.89; $^{19}$F {$^{13}$C} NMR (CDCl₃): δ −74.08. Anal. Calcd for C₁₀H₉F₃O₆S: C, 38.22; H, 2.89. Found: C, 38.43; H, 2.89.

3-Methoxybenzaldehyde (3a)

To a round-bottomed flask equipped with magnetic stirring bar was charged DMF (5 mL) and triethylamine (2.81 g, 27.8 mmol). Next, 98% formic acid (1.28 g, 27.8 mmol) was added dropwise over 1 min. Then, 2a (1 g, 3.5 mmol) was added followed by Pd(OAc)$_2$ (30 mg, 0.13 mmol) and DPPF (150 mg, 0.27 mmol). All the solids dissolved to give a clear orange solution. The mixture was then heated to 80° C. and after about 15 min a yellow solid precipitated. The mixture was cooled to room temperature and filtered. The filtrate was partitioned between Et$_2$O (25 mL) and H$_2$O (25 mL). The organic layer was further washed with H$_2$O (25 mL) followed by brine. The organic phase was dried over anhydrous MgSO$_4$ and evaporated under reduced pressure to yield a brown oil. Distillation under reduced pressure (0.1 torr) gave 3a as a colorless, mobile liquid (400 mg, 85%), lit. bp. 121° C./14 torr. $^1$H NMR (CDCl$_3$): δ 9.97 (s, 1H), 7.47-7.42 (m, 2H), 7.39-7.37 (m, 1H), 7.20-7.14 (m, 1H), 3.86 (s, 3H); $^{13}$C NMR (CDCl$_3$): δ 192.29, 160.38, 138.03, 130.22, 123.71, 121.70, 112.28, 55.67. Anal. Calcd for C$_8$H$_8$O$_2$: C, 70.57; H, 5.92. Found: C, 70.27; H, 5.95.

3,5-Dimethoxybenzaldehyde (3b)

To a round-bottomed flask (100 mL) equipped with magnetic stir bar and reflux condenser was charged DMF (3 mL) and triethylamine (1.29 g, 13 mmol). In dropwise fashion, 98% formic acid (0.588 g, 13 mmol) was added. Next, 2b (500 mg, 1.6 mmol) was added followed by Pd(OAc)$_2$ (35 mg, 0.15 mmol) and DPPF (177 mg, 0.3 mmol). All the solids dissolved resulting in a clear orange solution. The mixture was heated to 80° C. under an N$_2$ atmosphere. Shortly after heating, a yellow solid precipitated. After 1 h, the reaction mixture was cooled to room temperature and filtered through medium filter paper. The filtrate was partitioned between Et$_2$O (50 mL) and H$_2$O (50 mL). The organic layer was separated and washed with H$_2$O (25 mL) followed by brine (25 mL) The organic phase was separated and dried over anhydrous MgSO$_4$ and evaporated under reduced pressure leaving a yellowish solid which was essentially pure 3b (260 mg, 90%), mp. 42-44° C., lit. 45-46° C. $^1$H NMR (CDCl$_3$): δ 9.92 (s, 1H), 7.02 (d, J=2.2 Hz, 2H), 6.71 (t, J=2.2 Hz, 1H), 3.85 (s, 6H); $^{13}$C NMR (CDCl$_3$): δ 192.14, 161.49, 138.64, 107.41, 107.36, 55.88. And Calcd for C$_9$H$_{10}$O$_3$: C, 65.05; H, 6.07. Found: C, 65.39; H, 5.97.

trans-2-(4-Methoxyphenyl)-3-(3,5-dimethoxy-4-hydroxyphenyl)acrylic Acid (5)

To a round-bottomed flask (500 mL) equipped with magnetic stir bar and reflux condenser was charged 1b (9.1 g, 50 mmol), 4 (8.3 g, 50 mmol), Ac$_2$O (50 mL) and, lastly, triethylamine (10 g, 100 mmol, 2 equiv). The mixture was refluxed for 18 h. Afterwards, the hot reaction mixture was poured into vigorously stirred H$_2$O (300 mL). The precipitate formed was collected on a coarse porosity fitted glass filter. The filter cake was dissolved in 0.83 M NaOH (300 mL, 5 equiv). The mixture was filtered through a medium glass frit to remove a small amount of brown insoluble matter. The filtrate was then stirred and slowly acidified to pH 5 with conc. HCl. The tan precipitate formed was collected and dried in vacuo (10 ton, 40° C.) to give compound 5 as a tan powder (13.19 g, 79%). Pale yellow plates from EtOH, mp. 228-230° C. $^1$H NMR (DMSO): δ 12.43 (bs, CO$_2$H), 8.83 (bs, OH), 7.66 (s, 1H), 7.11 (d, J=8.6 Hz, 2H), 6.99 (d, J=8.6 Hz, 2H), 6.39 (s, 2H), 3.76 (s, 3H), 3.47 (s, 6H); $^{13}$C NMR (DMSO): δ 168.78, 158.66, 147.32, 139.69, 137.03, 130.94, 129.82, 129.07, 124.56, 114.12, 108.37, 55.41, 55.19. Anal. Calcd for C$_{18}$H$_{18}$O$_6$: C, 65.45; H, 5.49. Found: C, 65.18; H, 5.60.

1-Methylimidazolium p-Toluenesulfonate

To a round-bottomed flask (50 mL) equipped with magnetic stir bar was charged p-toluenesulfonic acid monohydrate (4.3 g, 23 mmol) followed by 1-methylimidazole (1.86 g, 23 mmol, 1 equiv). The mixture became warm as all the solids dissolved. After dissolution, water was removed under reduced pressure (10 ton to 1 torr, 60° C.) which gave a crude white solid. Recrystallization from EtOAc/MeCN gave the salt as a white microcrystalline powder (4.0 g, 69%), mp. 83-85° C., lit. 90-91° C. $^1$H NMR (CDCl$_3$): δ 9.09 (s, 1H), 7.76 (d, J=8.3 Hz, 2H), 7.31 (s, 1H), 7.20 (s, 1H), 7.15 (d, J=7.9 Hz, 2H), 3.88 (s, 3H), 2.34 (s, 3H); $^{13}$C NMR (CDCl$_3$): δ 142.73, 140.24, 136.24, 129.05, 125.92, 122.92, 120.36, 36.05, 21.41. Anal. Calcd for C$_{11}$H$_{14}$N$_2$O$_3$S.½ H$_2$O: C, 50.18; H, 5.74; N, 10.64. Found: C, 50.16; H, 5.52; N, 11.06.

trans-3,4',5-Trimethoxy-4-hydroxystilbene (6)

To a round-bottomed flask (500 mL) equipped with magnetic stir bar and reflux condenser was charged 1-methylimidazolium p-toluenesulfonate (34.8 g, 137 mmol, 5 equiv.) and 5 (9.1 g, 27.6 mmol). The mixture was stirred and heated to 130° C. (internal temperature) using a heating mantle. As the mixture reached temperature, the solids dissolved to a brownish colored solution and gas evolution (CO$_2$) was apparent. At 10 min intervals, a small aliquot of the reaction mixture was removed, dissolved in H$_2$O and extracted with Et$_2$O for TLC analysis. After heating for ~30 min, the mixture had a purplish color and TLC showed the reaction was complete. The mixture was cooled to ~90° C. and diluted with H$_2$O (300 mL) whereupon pinkish-tan colored solids precipitated. The precipitate was collected on a medium porosity fitted glass filter (7.57 g, 95%). The product was further purified by recrystallization from MeOH which gave compound 6 as rose colored needles, mp. 110-112° C., lit.[42] 96-98° C. $^1$H NMR (CDCl$_3$): δ 7.43 (d, J=8.7 Hz, 2H), 6.93-6.86 (m, 4H), 6.73 (s, 2H), 5.56 (bs, OH), 3.94 (s, 6H), 3.82 (s, 3H); $^1$H NMR (DMSO): 8.47 (s, OH), 7.49 (d, J=8.8 Hz, 2H), 7.07 (d, J=16.5 Hz, 1H), 6.97 (d, J=16.4 Hz, 1H), 6.93 (d, J=8.6 Hz, 2H), 6.85 (s, 2H), 3.81 (s, 6H), 3.76 (s, 3H); $^{13}$C NMR (CDCl$_3$): δ 159.18, 147.38, 134.69, 130.37, 129.37, 127.56, 126.88, 126.48, 114.25, 103.28, 56.39, 55.41; $^{13}$C NMR (DMSO): δ 158.55, 148.12, 135.40, 130.14, 127.92, 127.27, 126.78, 125.39, 114.15, 103.92, 55.98, 55.09. Anal. Calcd for C$_{17}$H$_{18}$O$_4$: C, 71.31; H, 6.34. Found: C, 71.11; H, 6.17.

trans-3,4',5-Trimethoxy-4-(trifluoromethanesulfonyloxy)stilbene (7)

To a round-bottomed flask (50 mL) equipped with magnetic stir bar and N$_2$ bubbler was charged 6 (600 mg, 2 mmol), pyridine (332 mg, 4 mmol, 2 equiv) and CH$_2$Cl$_2$ (20 mL) The mixture was cooled in an ice bath before Tf$_2$O (888 mg, 3 mmol, 1.5 equiv) was added dropwise over 20 min, during which the color changed from deep red to pale orange. Afterwards, the ice bath was removed and the reaction mixture was stirred at rt overnight. A work-up similar to that used in the preparation of 1a and 2a gave an oil that slowly crystallized in vacuo (790 mg, 90%). Recrystallization from heptanes/EtOAc gave compound 7 as clear, tan needles, mp. 104-106° C. (dec.). $^1$H NMR (CDCl$_3$): δ 7.46 (d, J=8.7 Hz, 2H), 7.03 (d, J$_{ab}$=16.1 Hz, 1H), 6.91 (d, J=8.7 Hz, 2H), 6.89 (d, J$_{ab}$=16.3 Hz, 1H), 6.72 (s, 2H), 3.93 (s, 6H), 3.84 (s, 3H); $^{13}$C NMR (CDCl$_3$): δ 160.00, 152.69, 138.64, 130.35, 129.59, 128.21, 125.75, 118.92 (q, $^1$J$_{CF}$=321.3 Hz), 114.49, 102.94, 56.49, 55.58; $^{19}$F {$^{13}$C} NMR (CDCl$_3$): δ −74.11. Anal. Calcd for C$_{18}$H$_{17}$F$_3$O$_6$S: C, 51.67; H, 4.10. Found: C, 51.84; H, 3.97.

trans-3,4',5-Trimethoxystilbene (8)

To a round-bottomed flask (100 mL) equipped with magnetic stir bar was charged anhydrous DMF (6 mL) and triethylamine (960 mg, 9.5 mmol, 5 equiv). In dropwise fashion, 98% formic acid (437 mg, 9.5 mmol, 5 equiv) was added over 10 min. After allowing the mixture to cool to room temperature, a previously prepared solution of 7 (790 mg, 2 mmol) in anhydrous DMF (3 mL) was added in one portion followed by Pd(OAc)$_2$ (21 mg, 0.09 mmol) and DPPF (105 mg, 0.18 mmol). A reflux condenser was equipped and the reaction mixture was heated under N$_2$ to an internal temperature of 80° C. After 20 min the mixture had become dark and the reaction was complete by TLC analysis. The mixture was cooled to room temperature and partitioned between H$_2$O (50 mL) and Et$_2$O (50 mL). A rag layer formed and the mixture was filtered through medium filter paper. The organic layer was separated and washed with H$_2$O (50 mL) and then brine (50 mL). After drying over anhydrous MgSO$_4$, evaporation of the organic phase under reduced pressure left a pale brown oil that slowly crystallized (470 mg, 91%), mp. 55-57° C., lit 56-57° C. $^1$H NMR (CDCl$_3$): δ 7.45 (d, J=8.9 Hz, 2H), 7.05 (d, J=16 Hz, 1H), 6.90 (d, J=16 Hz, 1H), 6.89 (d, J=8.6 Hz, 2H), 6.65 (d, J=2.2 Hz, 2H), 6.38 (t, J=2.5 Hz, 1H), 3.83 (s, 9H); $^{13}$C NMR (CDCl$_3$): 161.20, 139.93, 130.16, 128.96, 128.02, 126.81, 114.37, 104.57, 99.86, 55.57, 55.53. Anal. Calcd for C$_{17}$H$_{18}$O$_3$: C, 75.53; H, 6.71. Found: C, 75.53; H, 6.62. (E. Späth and K. Kromp, Ber., 74, 189 (1941)).

trans-3,4',5-Trihydroxystilbene (Resveratrol)

To a 250 mL round-bottomed flask equipped with a magnetic stir bar was added 8 (2.7 g, 10 mmol) and pyridine hydrochloride (10.4 g, 90 mmol, 9 equiv). A reflux condenser was equipped and the reaction mixture was refluxed for 2 h under an N$_2$ atmosphere. Afterwards, the mixture was allowed to cool to ~90° C. and quenched into H$_2$O (200 mL) whereupon a purplish colored solid precipitated. The mixture was extracted with EtOAc (50 mL×3). The extracts were collected and diluted with hexanes (100 mL) and then filtered through a thin pad of silica gel to remove dark colored, polar impurities. The filtrate was evaporated in vacuo leaving an off-white solid. The crude product was slurried with HOAc and filtered to give resveratrol as a tan microcrystalline powder (450 mg, 20%), mp. 258-261° C., lit. 261° C. $^1$H NMR (DMSO): δ 9.59 (s, OH), 9.23 (s, 2OH), 7.41 (d, J=8.9 Hz, 2H), 6.95 (d, J$_{ab}$=16.3 Hz, 1H), 6.82 (d, J$_{ab}$=16.3 Hz, 1H), 6.76 (d, J=8.9 Hz, 2H), 6.39 (d, J=2.0 Hz, 2H), 6.13 (t, J=2.1 Hz, 1H); $^{13}$C NMR (DMSO): δ 158.58, 157.28, 139.36, 128.15, 127.96, 127.92, 125.74, 115.61, 104.41, 101.87. Anal. Calcd for C$_{14}$H$_{12}$O$_3$: C, 73.67; H, 5.30. Found: C, 73.40; H, 5.44.

trans-3,4,4',5-Tetramethoxystilbene (9, DMU-212)

To a round-bottomed flask (100 mL) equipped with a magnetic stir bar and reflux condenser was charged 6 (1.16 g, 4.1 mmol) and anhydrous DMF (15 mL). The mixture was stirred until all the solids dissolved into a red solution then, in one portion, KOtBu (690 mg, 6.2 mmol, 1.5 equiv) was added. The color changed to fluorescent yellow-green and shortly thereafter copious solids precipitated (potassium salt of 6). Next, iodomethane (1.16 g, 8.2 mmol, 2 equiv) was added and the mixture was heated to 80° C. After 1 h, all the solids had dissolved and the color had become pale yellow. The mixture was cooled to room temperature and diluted with H$_2$O (50 mL) whereupon a white solid precipitated. The mixture was filtered on a medium porosity, fritted glass filter. The off-white filter cake was air dried on the frit (1.1 g, 89%). Recrystallization from heptanes/1,2-dichloroethane gave compound 9 as colorless plates, mp. 148-150° C., lit.[53] 152-153° C. $^1$H NMR (DMSO): δ 7.53 (d, J$_{ab}$=8.5 Hz, 2H), 7.17 (d, J$_{ab}$=16.1 Hz, 1H), 7.02 (d, J$_{ab}$16.3 Hz, 1H), 6.95 (d, J=8.5 Hz, 2H), 6.89 (s, 2H), 3.83 (s, 6H), 3.78 (s, 3H), 3.67 (s, 3H); $^{13}$C NMR (DMSO): δ 158.87, 153.04, 137.05, 133.12, 129.76, 127.59, 127.44, 126.29, 114.19, 103.61, 60.05, 55.86, 55.12. Anal. Calcd for C$_{18}$H$_{20}$O$_4$: C, 71.98; H, 6.71. Found: C, 71.84; H, 6.61.

Materials can be generated from a renewable phenol (syringaldehyde) that can be derived from lignocellulosic biomass. The use of syringaldehyde as a precursor to composites has the potential to reduce the cost and environmental impact of structural materials, while meeting or exceeding the performance of current petroleum derived resins.

Bisphenol compounds such as BPA (bisphenol A) are widely used as building blocks for a variety of commercial and industrial products. Specifically, bisphenols are the building blocks for polycarbonate plastics, epoxy resins, polyester resins, cyanate ester resins and other polymers/resins which include but are not limited to polycarbonates, polysulfones, polyesters, polyester-styrene, alkylphenolics, and polyalylates. Commercially available bisphenol compounds, especially polyaromatic bisphenols, are currently derived from petroleum.

In an effort to create more sustainable bisphenol building blocks we have developed a series of polyaromatic bisphenol compounds derived from syringaldehyde. Syringaldehyde can be isolated from crude biomass feedstocks that include lignin and the current invention describes a method to efficiently convert syringaldehyde into polyphenols. The ability to either homocouple syringaldehyde or cross-couple syringaldehyde with various renewable aldehydes allows for the synthesis of a variety of trifunctional and tetrafunctional bisphenols that can be converted to resins with exceptional glass transition temperatures. The utilization of renewable polyphenols as precursors to epoxies, polycarbonates, and high temperature thermosets including cyanate esters, provides an opportunity to develop full-performance resins while reducing the use of petroleum based feedstocks. This approach will then diminish the overall environmental impact of resin production while allowing for a sustainable source of phenols.

Some references in the literature include: CN 1736986 A describes the synthesis of 3,3'-5,5'-tetramethoxystilbene via a Wittig reaction; U.S. Pat. No. 4,087,336 describes electrochemical reduction of various p-benzaldehydes to stilbenes; and Dieguez, H. R. et al. J. Am. Chem. Soc. 2010, 132, 254-259 describes the synthesis of 3,3'-5,5' tetramethoxystilbene via Cp$_2$TiCl mediated reductive coupling.

1. Syringaldehyde is isolated from a renewable source (lignin). This step can include oxidation of lignin with oxygen, peroxides, or aromatic nitro-compounds among others. The oxidation step can be conducted with or without a transition metal catalyst. Syringaldehyde can also be recovered from the black liquor resulting from the Kraft pulping process.

2A. Syringaldehyde is directly coupled to a renewable aldehyde through chemical or electrochemical means. This step can be conducted via a transition metal mediated McMurry coupling or by applying a potential in a standard electrochemical setup to reductively couple the aldehydes.

3A. The reductively coupled product is converted to a polyphenol precursor by the following steps:
- 3Ai. Reductive coupling products generated by a McMurry reaction are hydrogenated to generate a saturated coupling product.
- 3Aii. The vicinal diols of reductive coupling products generated electrochemically are either reduced by hydrogenation or are protected and then reductively eliminated
- 3Aiii. Saturated coupling products are then converted to polyphenol precursors by dehydrodeoxygenation which is accomplished via conversion of phenols to sulfonates and subsequent reductive elimination with transition metal catalysts.

Alternate method for generation of polyphenol precursors:

2B. Syringaldehyde is converted to a reductive coupling product by:
- 2Bi. conversion to a sulfonate followed by reductive elimination to generate 3,5-dimethoxybenzaldehyde.
- 2Bii. 3,5-dimethoxybenzaldehyde is reductively coupled either by a transition metal mediated McMurry reaction or electrochemically to yield a reductive coupling product.

3B. Reductive coupling products are converted to polyphenol precursors by the following steps:
- 3Bi. Reductive coupling products generated by a McMurry reaction are hydrogenated to directly yield a polyphenol precursor.
- 3Bii. The vicinal diols of electrochemically generated reductive coupling products are either reduced by hydrogenation or are protected and then undergo reductive elimination to generate a polyphenol precursor.

4. Polyphenol precursors are converted to polyphenols by a demethylation reaction. Reagents for this step may include $BBr_3$ or pyridinium hydrochloride.

5. Polyphenols are converted to thermoplastics by methods known in the art.

6. Alternatively, polyphenols can be converted to resins including cyanate ester and epoxy resins.

7. Resins can be blended with support materials including glass or carbon fibers and thermally cured with or without a catalyst to generate a composite material.

The McMurry reaction is an organic chemical reaction under which two ketone or aldehyde groups combine to form an alkene in the presence of a titanium species resulting from reduction of a titanium (III or IV) compound with a reducing metal such as magnesium or zinc. The reaction may occur by a free radical process, similar to that observed in the pinacol coupling of aldehydes and ketones in the presence of a reducing metal, followed by an elimination of oxo-titanium species, owing to the strong bond that oxygen and titanium share. In some cases McMurry reactions can be catalytic with respect to titanium when stoichiometric chlorinating agents such as alkyl silyl chlorides are added to the reaction mixture. Other transition metal compounds based on tungsten are also effective at mediating McMurry reactions. The electrochemical coupling can be achieved by applying the appropriate voltage to a salt solution including the two ketone or aldehyde including compounds to form a coupled diol product. The reaction is run using a standard three electrode setup where the working and auxiliary electrodes are selected from lead, platinum, mercury, nickel, gold, or carbon; and performed at any voltage at which hydrogen evolution occurs at the chosen electrode. After the reaction the product diol is precipitated from the salt solution by acidification.

Syringaldehyde can be isolated from lignin or lignocellulosic feedstocks by chemical or enzymatic oxidation. It can also be prepared from other lignin decomposition products including vanillin. There are several methods available to couple syringaldehyde to other aldehydes. A direct chemical method including McMurry coupling can be utilized to combine the two aldehydes with generation of a double bond. Alternatively, an electrochemical method can be utilized to generate a diol. The diol can then be chemically reduced by various methods including hydrogenation or protection/deprotection through either chemical or electrochemical methods. In embodiments, the diol can be converted to a diacetate or oxalate and then reduced to the olefin electrochemically. When a mixture of aldehydes is utilized, a distribution of homocoupling and cross-coupling products will result. In some cases, the distribution can be controlled by the reactivity of a given aldehyde. The distribution can also in some cases be controlled by solubility. Mixtures of coupled products can be used directly or purified through various means including crystallization, column chromatography, distillation, and sublimation. Dehydrodeoxygenation can be accomplished by conversion of the phenol to a sulfonate (e.g. mesylate, tosylate, triflate). Reaction with zero valent nickel or palladium then results in reductive elimination. Both heterogeneous and homogenous catalysts are suitable for the reductive elimination. The methoxy groups can be converted to hydroxy groups by a variety of methods including reaction with boron tribromide ($BBr_3$) or pyridinium hydrochloride. Dehydrodeoxygenation is conducted as in steps described above. The resulting aldehyde is coupled as described above. In the case of electrochemical coupling of molecules with limited solubility in water, a non-aqueous solvent with a broad electrochemical window, including acetonitrile, is used and an additional hydrogen source must be introduced. Various resins can be prepared from the polyphenols by techniques known in the art. In embodiments, the polyphenols can be converted to cyanate esters by reaction with a suitable base and a cyanogen halide. Polyphenols can also be converted to epoxy resins by reaction with epichlorohydrin. Various thermoplastics can be prepared from the polyphenols by techniques known in the art. In embodiments, the polyphenols can be converted to polycarbonates by reaction with reagents including phosgene, triphosgene, and diphenylcarbonate. In other embodiments, thermoplastics including polysulfones, polyesters, polyester-styrene polymers, alkylphenolics, and polyalylates can be prepared from the polyphenols. Composites can be fabricated by combining resins or thermoplastics with various fibers (including carbon or glass fibers) and curing the composites through either thermal or chemical means.

In other embodiments, please see the schematics and reaction schemes herein. Scheme 1 illustrates the process by which syringaldehyde is first deoxygenated to 3,5-dimethoxybenzaldehyde in two steps. The phenol is converted to a mesylate, tosylate, or triflate. Then reductive elimination is achieved by reaction with zero valent nickel or palladium to produce the benzaldehyde. The 3,5-dimethoxybenzaldehyde is then used in the McMurry coupling reaction either alone or with another aldehyde or ketone to produce either the homo-coupled or hetero-coupled product, respectively. The coupled product is then hydrogenated under standard conditions with Pt, Pd, or Ni under ~40 psi of hydrogen. The saturated product is then demethylated using a catalyst including pyridinium hydrochloride or boron tribromide to give the polyphenol. The polyphenol is then reacted with cyanogen bromide or a similar cyanogen halide or pseudohalide and a base including triethylamine to yield the cyanate ester.

Scheme 2 illustrates the process by which syringaldehyde is first deoxygenated to 3,5-dimethoxybenzaldehyde in two steps. The phenol is converted to a mesylate, tosylate, or triflate. Then reductive elimination is achieved by reaction with zero valent nickel or palladium to produce the benzaldehyde. The 3,5-dimethoxybenzaldehyde is then used in an electrochemical coupling reaction either alone or with another aldehyde or ketone to produce either the homo-coupled or hetero-coupled diol product, respectively. The coupled product is then reduced either through hydrogenation, or protection and reductive elimination (chemically or electrochemically) to produce a polyphenol precursor. The polyphenol precursor is then demethylated using a catalyst including pyridinium hydrochloride or boron tribromide to give the polyphenol. The polyphenol is then reacted with cyanogen bromide or a similar cyanogen halide or pseudohalide and a base including triethylamine to yield the cyanate ester.

Scheme 3 illustrates the process by which syringaldehyde is first used in the McMurry coupling reaction either alone or with another aldehyde or ketone to produce either the homo-coupled or hetero-coupled product, respectively. The coupled product is then hydrogenated under standard conditions with Pt, Pd, or Ni under ~40 psi of hydrogen. The coupled products are then deoxygenated in two steps. Deoxygenation takes place by converting the phenol to a sulfonate (e.g. mesylate, tosylate, or triflate). Then reductive elimination is achieved by reaction with zero valent nickel or palladium to produce the polyphenol precursor. The deoxygenated product is then demethylated using a catalyst including pyridinium hydrochloride or boron tribromide to give the polyphenol. The polyphenol is then reacted with cyanogen bromide or a similar cyanogen halide or pseudohalide and a base including triethylamine to yield the cyanate ester.

Scheme 4 illustrates the process by which syringaldehyde is used in the electrochemical coupling reaction either alone or with another aldehyde or ketone to produce either the homo-coupled or hetero-coupled diol product, respectively. The coupled diol product is then reduced either through hydrogenation or protection and reductive elimination (chemically or electrochemically) to produce the saturated product. The coupled product is then deoxygenated in two steps. Deoxygenation takes place by converting the phenol to a sulfonate (e.g. mesylate, tosylate, or triflate). Then reductive elimination is achieved by reaction with zero valent nickel or palladium to produce the polyphenol precursor. The deoxygenated product is then demethylated using a catalyst including pyridinium hydrochloride or boron tribromide to give the polyphenol. The polyphenol is then reacted with cyanogen bromide or similar cyanogen halide and a base including triethylamine to yield the cyanate ester.

FIG. 1 is a flow chart showing methods to synthesize renewable precursors to high temperature thermosetting resins useful for fabrication of low-weight, composite aerospace structures.

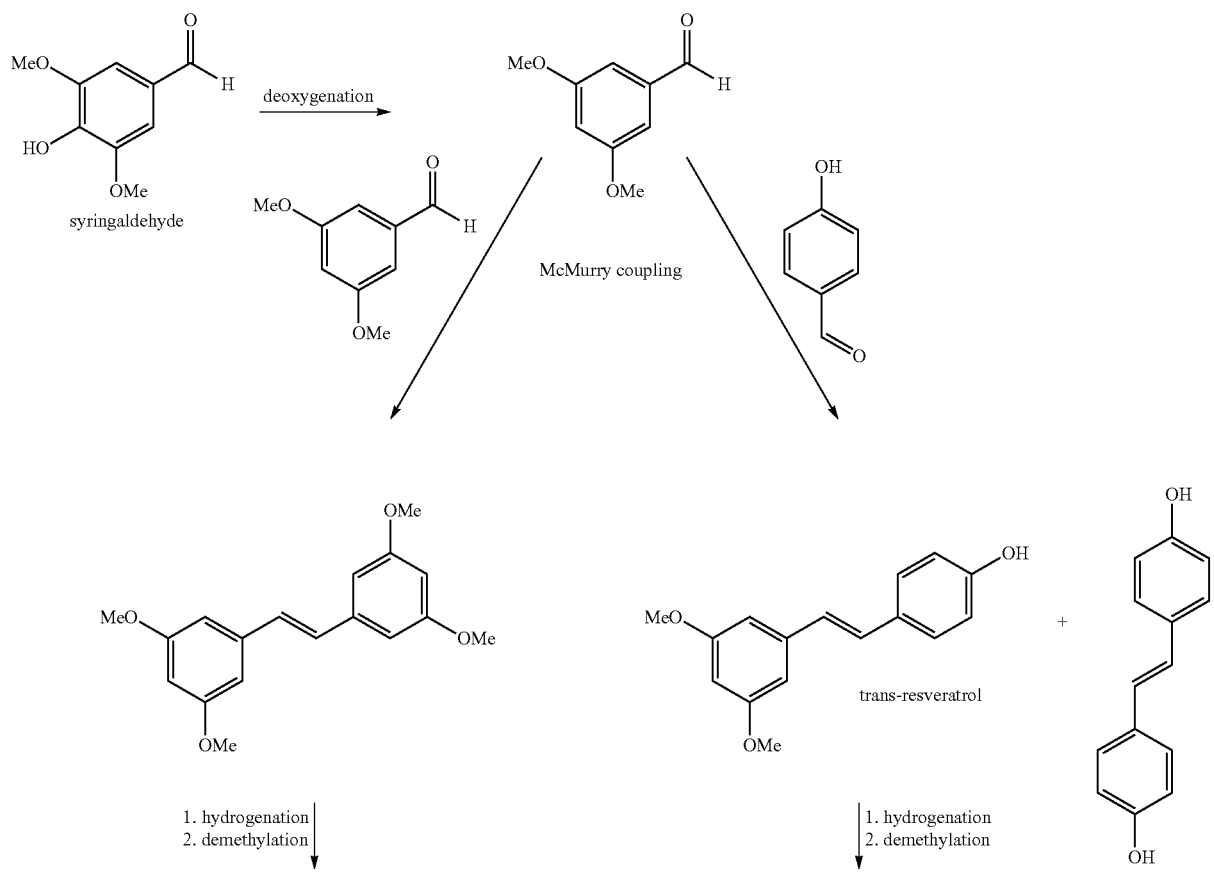

Scheme 1. Conversion of syringaldehyde to cyanate esters by initial dehydrodeoxygenation followed by a McMurry coupling.

17 18
-continued
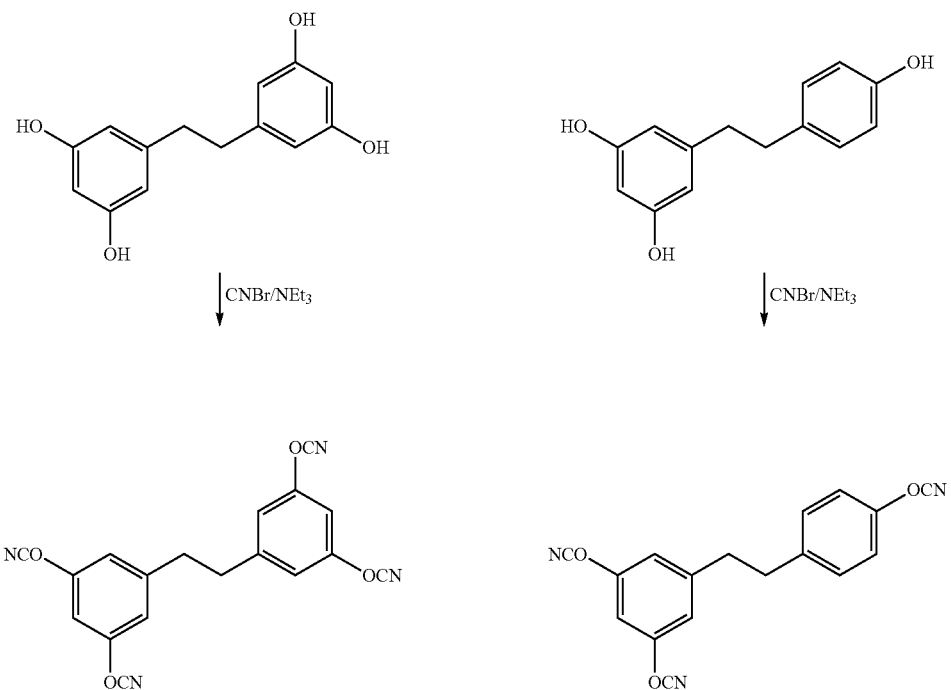
Scheme 2. Conversion of syringaldehyde to cyanate esters with initial dehydrodeoxygenation followed by a reductive electrochemical coupling
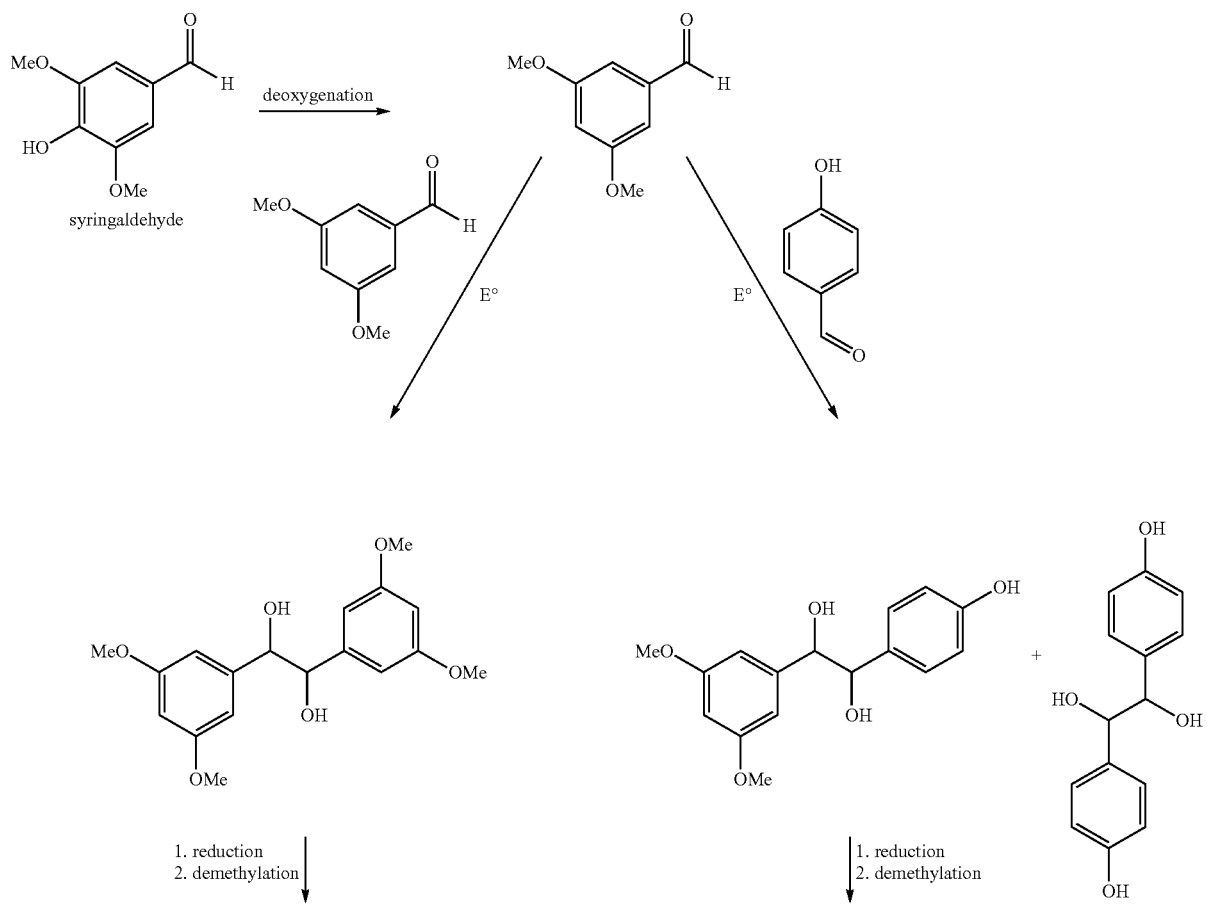

-continued
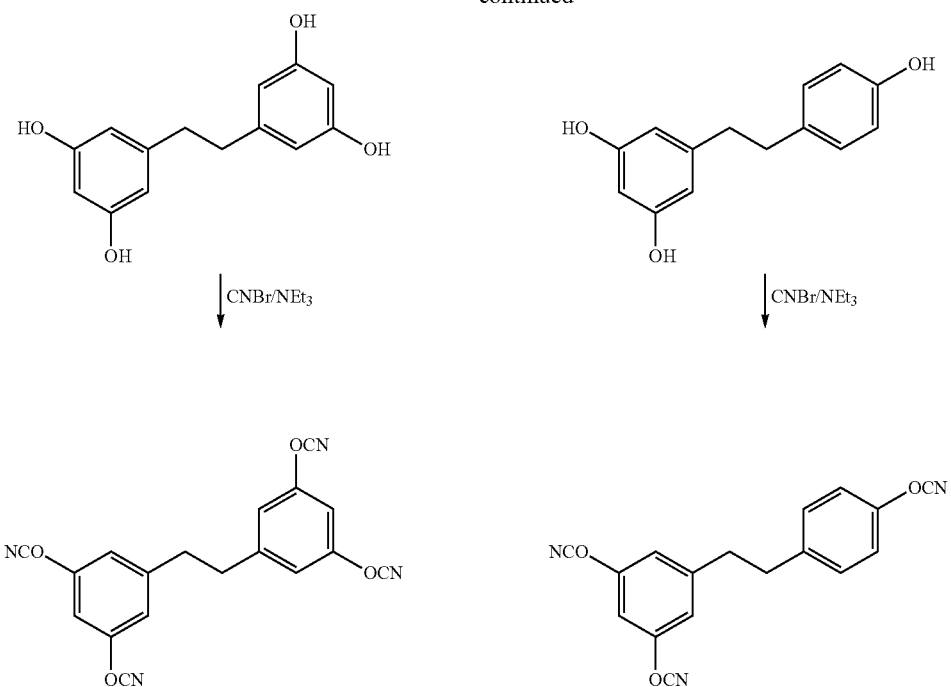
Scheme 3. Conversion of syringaldehyde to cyanate esters without initial dehydrodeoxygenation (McMurry coupling)
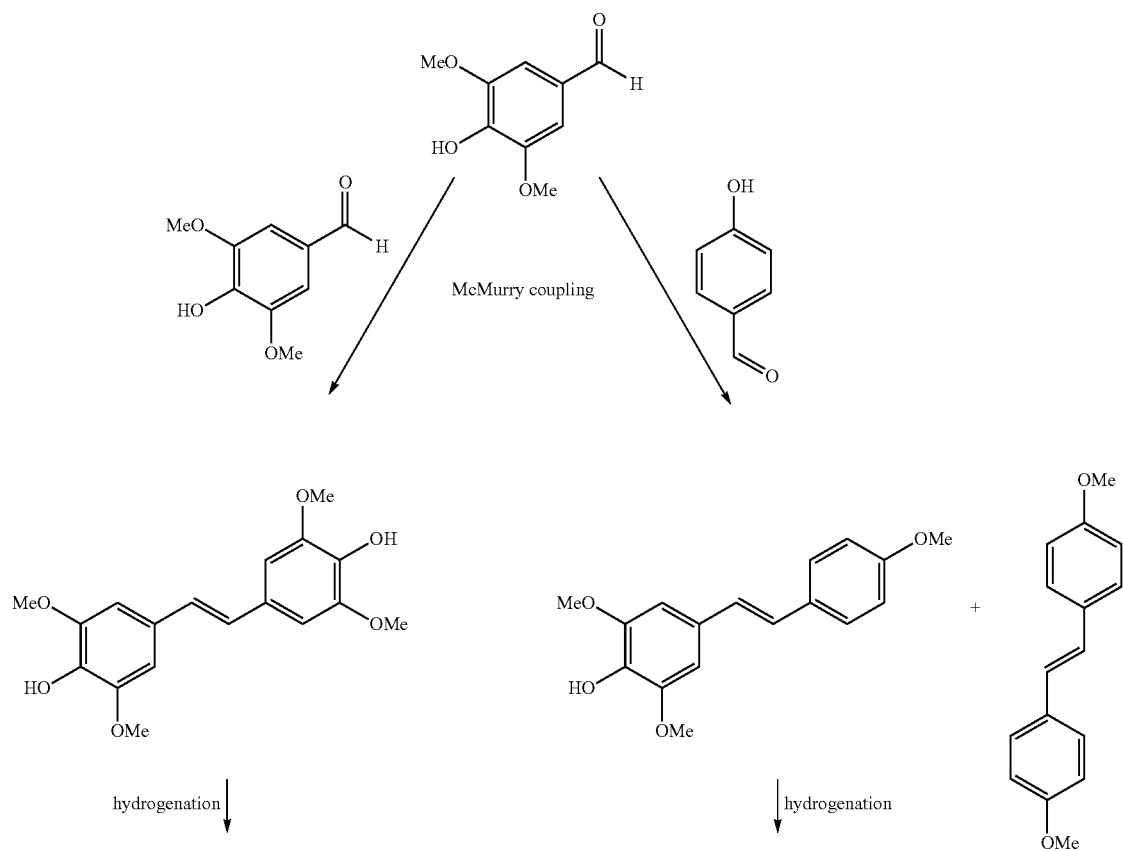

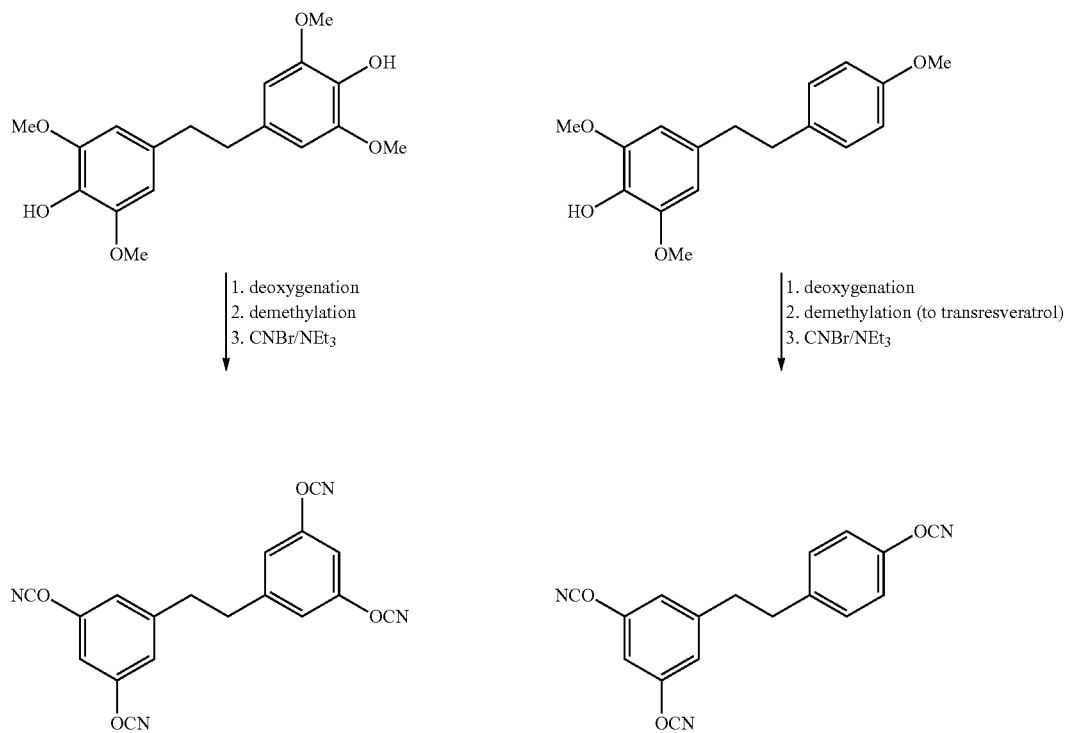
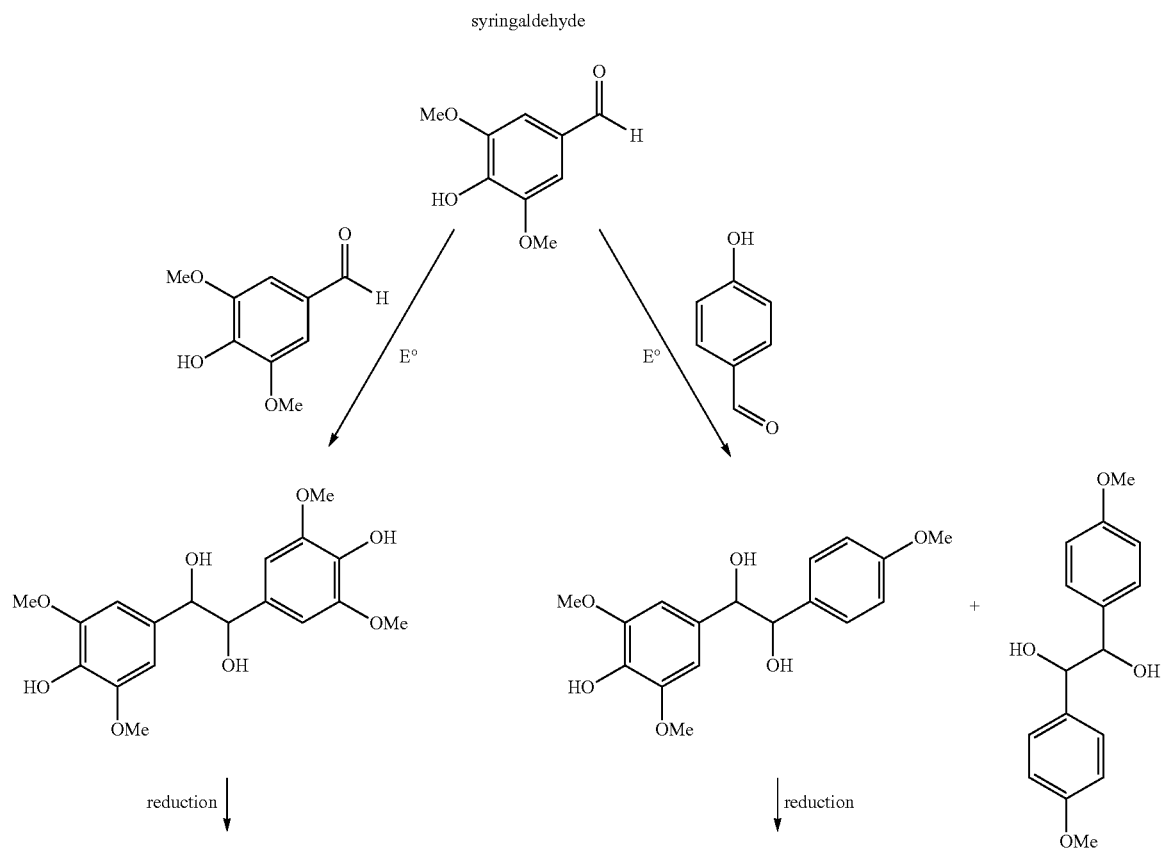
Scheme 4. Conversion of syringaldehyde to cyanate esters without initial dehydrodeoxygenation (electrochemical coupling)

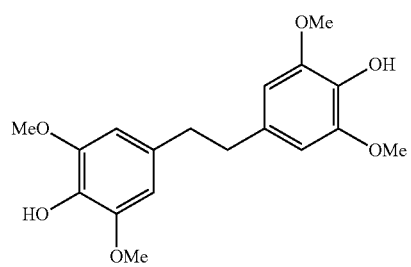

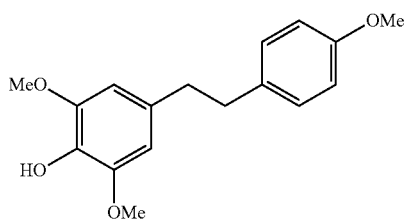

1. deoxygenation
2. demethylation
3. CNBr/NEt₃

1. deoxygenation
2. demethylation
3. CNBr/NEt₃

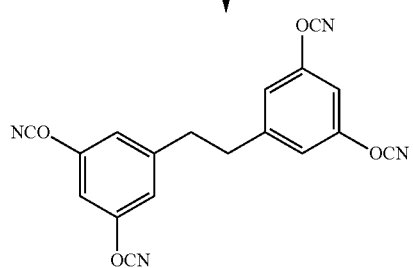

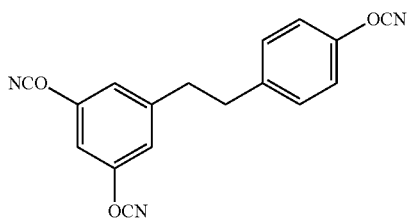

Embodiments of the invention generally relate to methods for making resins from syringaldehyde including, deoxygenating syringaldehyde by conversion to a sulfonate and reaction with a reductive elimination catalyst to produce 3,5-dimethoxybenzaldehyde, reductively coupling the dimethoxybenzaldehyde with at least one dimethoxybenzaldehyde or at least one aromatic aldehyde having a hydroxy group and/or methoxy group in at least one position on the aldehyde by a McMurry reaction or by reductive chemical or electrochemical reactions to produce at least one reductive coupling product, further reducing the reductive product(s) by hydrogenation, chemical reduction or electrochemical reduction followed by demethylating with a hydrolyzing reagent to produce polyphenols, and converting the polyphenols with a soluble base and cyanogen halide(s) or pseudohalides to produce cyanate ester resin(s).

An aspect of the invention generally relates to methods for making resins from syringaldehydes including, reductively coupling syringaldehyde with an additional molecule of syringaldehyde or at least one aromatic aldehyde having a hydroxy group, and/or methoxy group in at least one position on the aldehyde by a McMurry reaction or by reductive chemical or electrochemical reaction to produce at least one first reductive coupling product, further reducing the first reductive coupling product by hydrogenation or chemical reduction or electrochemical reduction to produce a second reductive coupling product, deoxygenating and demethylating the second reductive product(s) by conversion to a sulfonate followed by reaction with a reductive elimination catalyst and further reaction with a hydrolyzing reagent to produce polyphenols, and converting the polyphenols by reaction with a soluble base and cyanogen halide(s) or pseudohalides to produce cyanate ester resin(s). Other aspects of the invention further include thermoplastics, resins, and composites produced by the methods herein.

Embodiments further include converting the polyphenols by reaction with reagents including phosgene, triphosgene, diphenylcarbonate, other carbonates, bis(4-chlorophenyl) sulfone, other functionalized sulfones, diacid chlorides, phthalic acids, formaldehyde, other aldehydes, and epichlorohydrin to produce thermoplastics or resins selected from the group consisting of polysulfones, polyesters, polyesterstyrene polymers, alkylphenolics, polyarylates, polycarbonates, epoxy resins, and any combination thereof. In embodiments, the polyphenols are converted to thermosetting resins selected from the group consisting of cyanate ester resins, epoxy resins, benzoxazine resins, phenolic resins, bismaleimide resins, and polyether ether ketone (PEEK) resins. In embodiments, the resins are combined with the thermoplastics and fibers are thermally cured either with or without a catalyst to fabricate composite materials. In embodiments, the sulfonates are selected from the group consisting of mesylates, tosylates and triflates. In embodiments, the reductive elimination catalyst is selected from the group including zero valent nickel or palladium catalysts. In embodiments, the McMurry reaction includes catalysts selected from the group consisting of reducible titanium(III) or titanium(IV) compounds and reducing agents selected from the group consisting of lithium, sodium, potassium, zinc dust, zinc copper couple, magnesium, magnesium-mercury amalgam, and lithium aluminum hydride. In embodiments, the reductive coupling product produced by the McMurry reaction includes stilbenes. In embodiments, the stilbene is trans-resveratrol or cis or trans-3,3'-5,5'-stilbenetetrol.

In embodiments, the electrochemical coupling was accomplished using electrodes selected from the group consisting of lead, platinum, mercury, nickel, gold, and carbon and performed at a voltage at which hydrogen evolution occurs at the chosen electrode. In embodiments, the reductive coupling product produced by the reductive chemical or reductive electrochemical reaction results in a linking group between aromatic rings that selected from the group consisting of vicinal diols, alkenes, ketones, alcohols, and alkanes. In embodiments, hydrogenation is achieved by using a catalyst that include a transition metal selected from the group consisting of platinum, palladium, nickel, ruthenium, molybdenum, copper, and chromium and is conducted under a gas including hydrogen atmosphere.

In embodiments, the chemical reduction is achieved by protection of the vicinal diol to the diacetate or oxolate followed by reduction to a stilbene using the base with or without a reducing metal including zinc or magnesium. In embodiments, the electrochemical reduction is achieved by initial conversion of the vicinal diol to an oxalate or acetate followed by electrochemical reduction. In embodiments, the hydrolyzing reagent is selected from the group consisting of pyridinium hydrochloride, boron tribromide and other suitable reagents. In embodiments, the base is selected from the group consisting of alkyl amines including triethylamine, alkali and alkaline earth alkoxides, and other suitable bases. In embodiments, the cyanogen halide is selected from the group consisting of cyanogen bromide, cyanogen chloride, cyanogen iodide, and any combination thereof. In embodiments, the cyanogen pseudohalide is a cyanogen sulfonate, wherein the sulfonates are defined as $RSO_3^-$ (R=at least one alkyl or aromatic group).

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for selective deoxygenation of hydroxybenzaldehydes, comprising:
    condensing syringaldehyde (3,5-dimethoxy-4-hydroxybenzaldehyde) and a functionalized phenylacetic acid with at least one first base and at least one anhydride to produce an arylcinnamic acid;
    decarboxylating of said arylcinnamic acid with at least one decarboxylation catalyst at temperatures ranging from about 30° C. to about 200° C. or thermally from about 100° C. to about 350° C. to produce first stilbene(s);
    hydrodeoxygenating said stilbene(s) by conversion to sulfonate(s) in the presence of at least one second base in water or at least one organic solvent to yield sulfonate(s);
    reducing said sulfonate(s) with a reductive elimination catalyst to produce a second stilbene(s); and
    reacting said second stilbene(s) with a hydrolyzing agent to generate a polyphenol.

2. The method according to claim 1, wherein said functionalized phenylacetic acid is 4-methoxyphenylacetic acid.

3. The method according to claim 1, wherein said arylcinnamic acid is 2-arylcinnamic acid.

4. The method according to claim 1, wherein said decarboxylation catalyst is selected from the group consisting of p-toluenesulfonate, Cu-based catalysts, Ag-based catalysts, amine catalysts, and any combination thereof.

5. The method according to claim 1, wherein said reductive elimination catalyst is selected from a group consisting of low valent Ni or Pd compounds.

6. The method according to claim 1, wherein said first stilbene(s) are trans-isomer(s).

7. The method according to claim 1, wherein said phenylacetic acid has one or more hydroxy or alkoxy groups at any position on the aromatic ring.

8. The method according to claim 1, wherein said first and/or said second base is selected from the group consisting of aromatic amines, alkyl amines, alkali or alkaline earth alkoxides, phosphates, carbonates, and any combination thereof.

9. The method according to claim 1, wherein said organic solvent is selected from the group consisting of chloroform, diethyl ether, tetrahydrofuran, other solvents capable of dissolving aromatic triflates and any combination thereof.

10. The method according to claim 1, wherein said second stilbene(s) is resveratrol trimethyl ether.

11. The method according to claim 1, wherein said hydrolyzing agent is selected from the group consisting of molten pyridine hydrochloride, mineral acids, $BBr_3$, and $BCl_3$.

12. The method according to claim 1, further comprising methylating said first stilbene(s) with an alkali alkoxide and iodomethane to produce (E)-3,4,5,4'-tetramethoxystilbene.

13. The method according to claim 3, wherein said 2-arylcinnamic acid is

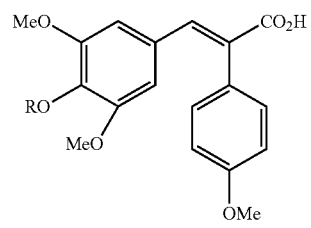

7a R = Ac
7b R = H wherein R is acetyl or hydrogen; and
wherein said sulfonate(s) is

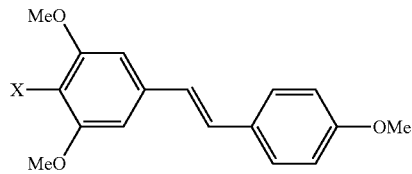

wherein x is selected from the group consisting of $-OSO_2CH_3$, $-OSO_2(C_6H_4)CH_3$, and $OSO_2CF_3$.

14. The method according to claim 1, wherein said polyphenol is selected from the group consisting of trans-Resveratrol or (E)-3,4'5-trimethoxy-4-hydroxystilbene (DMU-291).

* * * * *